United States Patent [19]

Schuster et al.

[11] Patent Number: 5,622,982
[45] Date of Patent: Apr. 22, 1997

[54] ACYLATED AMINOALKANIMIDAZOLES AND - TRIAZOLES

[75] Inventors: Ingeborg Schuster; Helmut Egger, both of Vienna, Austria

[73] Assignee: Sandoz Ltd., Basel, Switzerland

[21] Appl. No.: 442,053

[22] Filed: May 16, 1995

[30] Foreign Application Priority Data

May 18, 1994 [GB] United Kingdom ............... 9409882

[51] Int. Cl.⁶ .................. A61K 31/415; C07D 401/12; C07D 409/12; C07D 233/61
[52] U.S. Cl. ............ 514/399; 514/341; 514/397; 546/275.1; 548/315.1; 548/338.1
[58] Field of Search .................. 548/338.1, 315.1; 514/399, 341, 397; 546/275.1

[56] References Cited

U.S. PATENT DOCUMENTS 3,796,704  3/1974  Metzger et al. .
4,191,767  3/1980  Warner, Jr. et al. .

FOREIGN PATENT DOCUMENTS

3408127A1  9/1984  Germany .
2136801    9/1984  United Kingdom .
2199579    7/1988  United Kingdom .

OTHER PUBLICATIONS

European Patient Office Patent Abstracts JP4005287 —Sep. 1, 1992 —Page 1 of 1.
Chem. Abstract 108:21901 vol. 108, 1988 —2 pages.

Primary Examiner—Patricia L. Morris
Attorney, Agent, or Firm—Robert S. Honor; Melvyn M. Kassenoff; Thomas O. McGovern

[57] ABSTRACT

The invention concerns azole compounds of formula

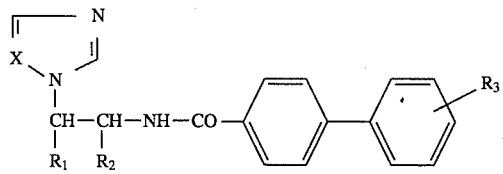

wherein the substituents have various significances, in free form or salt form.

They can be prepared e.g. by acylation, or by aziridine or oxazole ring opening.

The compounds can be used as pharmaceuticals, especially as selective inhibitors of the 25-hydroxyvitamin D3—hydroxylases in the treatment of disorders of proliferation and differentiation in vitamin D—responsive tissues.

16 Claims, No Drawings

ACYLATED AMINOALKANIMIDAZOLES AND -TRIAZOLES

The invention relates to acylated aminoalkylimidazole and -triazole derivatives.

More particularly, the invention concerns compounds of the formula

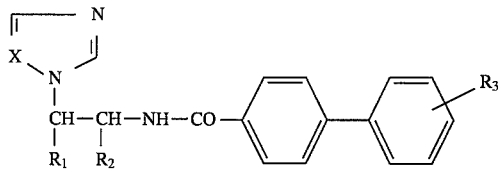

wherein either $R_1$ represents phenyl, naphthyl, thienyl or pyridyl, whereby these four substituents are optionally monosubstituted by halogen, alkoxy, alkyl, dialkylamino or cyano and $R_2$ represents hydrogen; or $R_1$ represents hydrogen and $R_2$ represents pyridyl or 2-(5-chloro)pyridyl; $R_3$ represents hydrogen, halogen, alkyl, cyano, alkoxycarbonyl, alkylcarbonyl or optionally substituted amino; and X represents CH or N; in free form or salt form, hereinafter briefly named "the compounds of the invention".

$R_1$ preferably is phenyl. When it is other than phenyl it preferably is hydrogen. $R_2$ preferably is hydrogen. $R_3$ preferably is halogen. It preferably is in 4 position. X preferably is CH.

When $R_1$ is other than hydrogen it preferably is unsubstituted. When phenyl is substituted it preferably is substituted in 4 position. When pyridyl is substituted it preferably is substituted in 5 position.

Halogen is fluorine, chlorine, bromine or iodine, preferably chlorine. Alkoxy and/or alkyl and/or the alkyl substituents in dialkylamino and/or the alkoxy part in alkoxycarbonyl and/or the alkyl part in alkylcarbonyl preferably are independently of 1 to 4, especially 1 or 2, particularly 1 carbon atom(s). Optionally substituted amino preferably is unsubstituted. When it is substituted it preferably is disubstituted, preferably by alkyl of 1 to 4 carbon atoms.

Pyridyl preferably is 2- or 4-pyridyl. Naphthyl preferably is 1-naphthyl.

Calcitriol [1,25(OH)$_2$D3], the most potent hormonal form of vitamin D3 (D3)—which acts in the manner of steroidal hormones—plays an important regulatory role in switching cells from proliferation towards differentiation, in calcium homeostasis and in immune regulation. Epidermal keratinocytes possess specific calcitriol receptors and respond to the hormone in vitro by a reduction of proliferation and induction of terminal differentiation. In vivo topical calcitriol (and several analogues) exerts beneficial therapeutic effects in the treatment of hyperproliferative inflammatory skin disorders such as psoriasis: its efficacy may be at least partially explained by its antiproliferative/prodifferentiating effects on keratinocytes but also by its immunosuppressive action on invading inflammatory cells. In addition, some observations point to a specific role of vitamin D—metabolites also in the regulation, remodelling and function of the dermal connective tissue: calcitriol inhibits fibroblast proliferation at pharmacological doses, elevates collagen I and III levels—the two main dermal connective tissue constituents—and upregulates the human elastin promoter in vivo. Moreover, calcitriol appears to play a crucial role in the regulation of hair growth and prevention of chemotherapy-induced alopecia, as indicated e.g. by changing calcitriol receptor expression during the hair cycle.

In spite of the desirable pleiotropic effects of calcitriol and analogues on skin, side effects of topical therapy such as skin irritation in some 10% of patients and especially hypercalcemia are noticed in psoriatic patients with extended skin involvement. Concerns about toxicity arising from topical treatment of large body areas with calcitriol or analogues thereof exist and long term safety data have not yet been established.

However, since psoriasis gradually recurs upon interruption of treatment, life-long therapy has to be anticipated.

The present invention provides the beneficial effects of calcitriol in skin while avoiding the negative side effects of its topical application by the following approach:

Keratinocytes themselves are capable of high calcitriol synthesis from the precursor 25(OH)D3 via vitamin D1—hydroxylase [Bikle et al. (1986) infra] and are therefore both source and target for the hormone. Calcitriol controls its levels tightly by rapidly upregulating vitamin D—hydroxylases (e.g. the vitamin D—24-hydroxylase) which attack different positions of its C20–27 side chain and via a cascade of sequential metabolites eventually terminates its action. The compounds of the present invention specifically inhibit particular steps of this cascade without major interference with calcitriol synthesis. As a consequence selective inhibition of particular steps of calcitriol catabolism increases and prolongs endogenous local levels of calcitriol (and of some other hormonally active metabolites) and thereby potentiates its (their) desirable effects on keratinocyte proliferation and differentiation. Increased and prolonged stationary local levels of calcitriol exert beneficial effects on local inflammatory/allergy confering cells, on hair growth regulation and on the regulation and function of the dermal connective tissue, whereby, due to the high but limited capacity for local calcitriol synthesis, the undesired side effects observed after application of pharmacological doses are avoided.

A group of compounds of the invention is the compounds of the formula

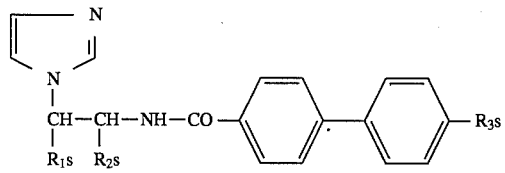

wherein
either $R_1s$ represents phenyl, phenyl monosubstituted by halogen or 1-naphthyl and $R_2s$ represents hydrogen; or
$R_1s$ represents hydrogen and $R_2s$ represents pyridyl or 2-(5-chloro)pyridyl; and $R_3s$ represents halogen or alkoxy of 1 to 4 carbon atoms; in free form or salt form.

In a subgroup of compounds of formula Is $R_3s$ chlorine. In a further subgroup $R_3s$ is alkoxy of 2 to 4 carbon atoms. In a further subgroup phenyl monosubstituted by halogen is phenyl monosubstituted by chlorine, preferably in 4 position. In a further subgroup $R_1s$ represents phenyl or, preferably, phenyl monosubstituted by chlorine in 4 position; $R_2s$ represents hydrogen; and $R_3s$ represents chlorine in 4 position.

A further group of compounds of the invention is the compounds of formula Ip

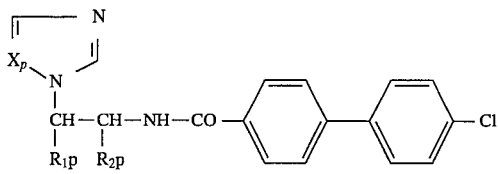

wherein
either $R_1p$ represents phenyl optionally monosubstituted by chlorine in 4 position and $R_2p$ represents hydrogen
or $R_1p$ represents hydrogen and $R_2p$ represents 2-(5-chloro)pyridyl, and
Xp represents CH or N;
or $R_1p$ represents 1-naphthyl, $R_2p$ represents hydrogen and Xp represents CH;
in free form or pharmacologically acceptable acid addition salt form.

The compounds of the invention may be prepared by a process comprising
a) acylating corresponding compounds of the formula

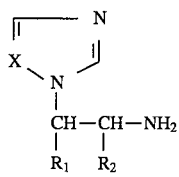 II wherein the substituents are as defined above, to introduce a corresponding biphenyl-4-carbonyl group; or
b) for the preparation of compounds of the formula

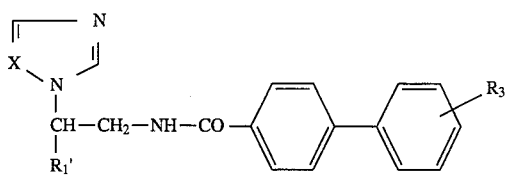 Ia wherein $R_3$ and X are as defined above and $R_1'$ has the same significance as $R_1$ as defined above excluding hydrogen, reacting corresponding compounds of the formula

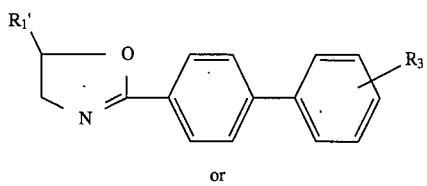 III or

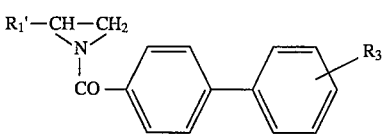 IIIa wherein $R_1'$ and $R_3$ are as defined above, with the corresponding compound of the formula

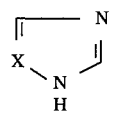 IV wherein X is as defined above;
and recovering the resultant compounds of formula I in free form or salt form.

The process of the invention can be effected in conventional manner.

Process variant a) may for example be carried out by reacting a compound of formula II with an appropriate acyl halide in a solvent, e.g. in an organic or inorganic base which may at the same time act as an acid binding agent, such as pyridine, optionally with addition of an acylation accelerator such as 4-dimethylaminopyridine. The reaction may also be carried out by reacting a compound of formula II with an appropriate active ester or a further activated acyl derivative, e.g. a mixed anhydride or an imidazolide available by using N,N-carbonyl-diimidazole as a reagent. The reaction can thus for example be carried out with a 2-pyridyl-thiol ester such as 4'-chlorobiphenyl-4-carboxylic acid-2-pyridyl-thiol ester in an inert solvent such as a di-lower alkyl carboxylic acid amide, e.g. dimethylformamide, preferably at room temperature.

Process variant b) may be carried out by mixing a compound of formula III or IIIa with a compound of formula IV and heating the mixture to elevated temperature, e.g. to about 120° C.

The starting materials are either known or may be prepared according to known procedures or analogously to known procedures or analogously as described herein, e.g. in the examples.

The compounds of formula II may e.g. be prepared according to the following reaction scheme:

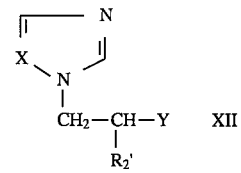 XII

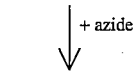

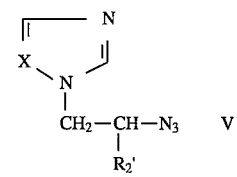 V

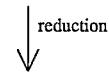

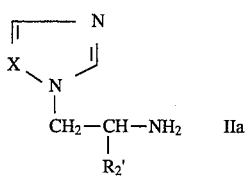 IIa

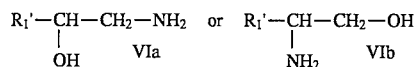

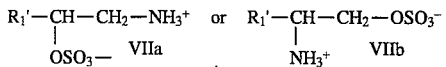

-continued

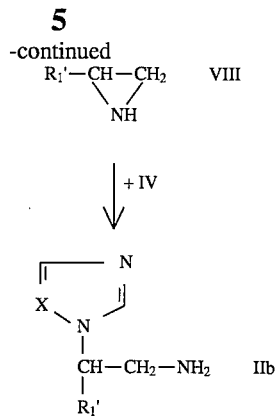

In the above reaction scheme $R_2'$ has the same significance as $R_2$ as defined above excluding hydrogen, Y represents halogen, preferably chlorine, and the other substituents are as defined above.

The starting materials of formula III may e.g. be prepared according to the following reaction scheme:

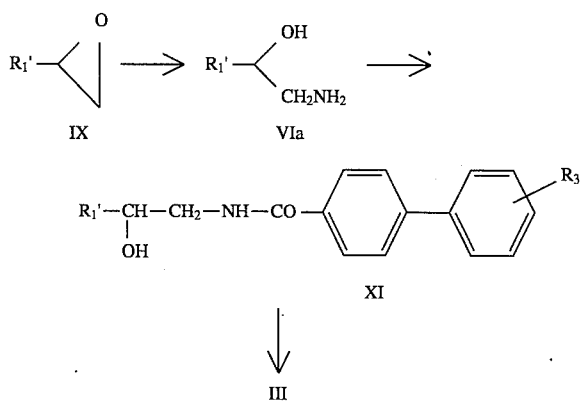

In this reaction scheme the substituents are as defined above.

The starting materials of formula IIIa may e.g. be prepared by appropriately acylating a corresponding compound of formula VIII.

The compounds of formula I are chiral at the carbon atom carrying a group $R_1$ or $R_2$ other than hydrogen and accordingly they can exist as racemates, pure enantiomers [(R) and (S)] or mixtures thereof. The invention provides all stereoisomers as well as racemic mixtures. The isomers may be resolved or separated by conventional techniques, e.g. chromatographically.

The preparation of the pure enantiomers of the compounds of formula I preferably is effected by using pure enantiomers as starting materials in process variants a) and b). Ring opening of enantiomerically pure aziridine compounds of formula VIII or IIIa upon reaction with a compound of formula IV proceeds by inversion of the configuration to give a compound of formula IIb or Ia with the opposite configuration. Furthermore in the reaction step leading from the compounds of formula XI to the compounds of formula III and in the following step to the compounds of formula Ia inversion of the configuration also occurs. In all other reaction steps for the reactions described above the configuration remains unchanged. Therefore, using enantiomerically pure starting materials results in end products with the opposite configuration when one reaction step is used which inverts the configuration at the chirality center, but results in end products with unchanged configuration when either no reaction step, or two reaction steps are used which invert the configuration at the chirality center.

The single steps of these reactions may be carried out in conventional manner.

A compound of the invention can be in free form or salt, such as acid addition salt form. A compound of the invention in free form can be converted into a salt, such as an acid addition salt form thereof, e.g. the hydrochloride or the nitrate, in conventional manner and vice-versa.

The following abbreviations are used hereinafter:

| | |
|---|---|
| 25(OH)D3: | 25-hydroxyvitamin D3 |
| 1,25(OH)₂D3: | 1,25-dihydroxyvitamin D3 (calcitriol) |
| 24,25(OH)₂D3: | 24,25-dihydroxyvitamin D3 |
| 1,24,25(OH)₃D3: | 1,24,25-trihydroxyvitamin D3 |
| 1,23,25(OH)₃D3: | 1,23,25-trihydroxyvitamin D3 |
| DMF | dimethylformamide |
| DMSO | dimethyl sulfoxide |
| HPLC: | high performance liquid chromatography |
| THF | tetrahydrofuran |
| b.p. | boiling point |
| dpm | disintegrations per minute |
| m.p. | melting point |
| EGF | epidermal growth factor |
| FCS | fetal calf serum |
| HBSS | Hank's balanced salt solution |
| KGM | keratinocyte growth medium (Clonetics, San Diego, CA, USA) |

All temperatures are given herein in degrees centigrade. The following examples illustrate the invention but are not limitative.

EXAMPLE 1

1-(5-Chloro-2-pyridyl)-2-(1H-imidazol-1-yl)-N-[4-(4-chlorophenyl)benzoyl]-1-aminoethane

[process variant a)]

To a solution of 0.44 g of 1-amino-1-(5-chloro-2-pyridyl)-2-(1H-imidazol-1-yl)ethane in 1 ml of dimethylformamide is added a solution of 0.645 g of 4'-chlorobiphenyl-4-carboxylic acid-2-pyridyl-thiol ester in 2 ml of dry dimethylformamide. The reaction mixture is stirred at room temperature and under argon for 18 hours. The reaction mixture is poured onto cold saturated brine and extracted with ethyl acetate. The combined organic phases are washed with brine, dried over $Na_2SO_4$, filtered and the solvent is evaporated (=working up process A). Treatment of the crude product with diethylether gives the title compound as colourless crystals; m.p.: 143°–146°.

Using optically active enantiomers as starting material and proceeding as described above yields the corresponding optically active enantiomers of the title compound:
(+)-enantiomer: $[\alpha]_D^{20}=+6.7°$ (c=0.52, methanol); m.p.: 175°–186°
(−)-enantiomer: $[\alpha]_D^{20}=−7.0°$ (c=0.52, methanol); m.p.: 175°–186°.

Analogously as described in example 1 the following compounds of formula I are obtained (X=CH, $R_1$=H) according to process variant a), in racemic form:

| Example | $R_2$ | $R_3$ | m.p. |
|---|---|---|---|
| 2 | 2-pyridyl | 4-Cl | 165–166° |
| 3 | 3-pyridyl | 4-Cl | 215–218° |
| 4 | 4-pyridyl | 4-Cl | 185–191° |
| 5 | 5-Cl-2-pyridyl | 4-OC₂H₅ | 170–184° |
| 6 | 5-Cl-2-pyridyl | 4-OC₄H₉ | 152–155° |

EXAMPLE 7

N-[4-(4-Chlorophenyl)benzoyl]-2-(1H-imidazol-1-yl)-2(S)-phenyl-1-aminoethane

[process variant a)]

The solution of 0.96 g of crude (S)-2-phenyl-2-(1H-imidazol-1yl)-1-aminoethane in 5 ml of N,N-dimethylformamide is charged, with stirring, with 1 g of 4'-chlorobiphenyl-4-carboxylic acid-2-pyridyl-thiol ester. After 6 hours the reaction mixture is quenched by pouring into cold water (0°, 50 ml). The precipitate is extracted with ethyl acetate, the organic phase is washed with brine, dried over magnesium sulfate and evaporated. The crystalline residue is triturated with ethanol, filtered by suction and washed with cold ethanol. Drying of the crystals yields the pure title compound; m.p.: 176°–177°; $[\alpha]_D^{20}$=+17.8° (c=1.2, methanol). The filtrate is evaporated and purification by chromatograply over silica gel (dichloromethane/methanol/heptane=7/1/4) provides additional pure material of the title compound.

The (R)-enantiomer of the title compound is prepared analogously starting from (R)-2-phenyl-2-(1H-imidazol-1-yl)-1-aminoethane; m.p.: 176°–179°; $[\alpha]_D^{20}$=−17.4° (c=1.1, methanol).

EXAMPLE 8

N-[4-(4-Chlorophenyl)benzoyl]-2-(1H-imidazol-1-yl)-2(S)-phenyl-1-aminoethane

[process variant b)]

0.398 g of N-(4'-chlorobiphenyl-4-carbonyl)-2(R)-phenyl-aziridine are mixed with 0.15 g of imidazole and heated at 110° for 16 hours. After cooling the solid residue is dissolved in 1.5 ml of DMF by warming. The solution is poured into ice water. The precipitated solid is collected by suction, washed with water and dried. The material is purified by chromatography on silica gel (toluene/ethanol= 8/1). The title compound is obtained as white crystals; m.p.: 176°–179°; $[\alpha]_D^{20}$=+19.6° (c=1.0, methanol);

$^1$H-NMR (DMSO-$d_6$) δ=8.82 (t, J=5.3 Hz; 1H); 7.87–7.84 (m; 3H); 7.78–7.74 (m; 4H); 7.55 (d, J=8.5 Hz; 2H); 7.41–7.30 (m; 6H); 6.92 (s; 1H); 5.70 (dd, J=6.0, 9.1 Hz; 1H); 4.16–3.94 (m; 2H).

EXAMPLE 9

N-[4-(4-Chlorophenyl)benzoyl]-2-(1H-imidazol-1-yl)-2(R)-phenyl-1-aminoethane

[process variant b)]

380 mg of 2-(4'-chlorobiphenyl-4-yl)-5(S)-phenyl-4,5-dihydro-oxazole and 775 mg of imidazole are heated at 120° for 23 hours. Ethyl acetate and water are added, the organic layer is washed three times with water, dried over magnesium sulfate and concentrated in vacuo. After addition of toluene the title compound precipitates as colourless crystals; m.p.: 176°–179° (recrystallized from toluene); $[\alpha]_D^{20}$= −17.4° (c=1.1, methanol). The $^1$H-NMR spectrum is identical with the spectrum for the S (+)-enantiomer in example 8.

Analogously as described in example 8 the following compounds of formula I are obtained according to process variant b), in racemic form:

| Example | X | $R_1$ | $R_2$ | $R_3$ | m.p. |
|---|---|---|---|---|---|
| 10* | CH | 4-Cl—$C_6H_4$ | H | 4-Cl | 229–234° |
| 11 | CH | 1-naphthyl | H | 4-Cl | 227–230° |

*The 2(S)-enantiomer of the compound of example 10 is obtained analogously as described in example 9 from the corresponding 4,5-dihydro-oxazole; m.p. 197–204°; $[\alpha]_D^{20}$ = +1.1° (c = 0.49, chloroform).

EXAMPLE 12

N-[4-(4-Chlorophenyl)benzoyl]-2-(1H-imidazol-1-yl)-2-phenyl-1-aminoethane

[process variant a)]

0.94 g of 2-phenyl-2-(1H-imidazol-1-yl)-1-aminoethane are acylated with 0.17 g of 4'-chlorobiphenyl-4-carboxylic acid-2-pyridyl-thiol ester analogously as described in example 1. Chromatography on silica gel (dichloromethane/methanol/aqueous NH$_3$/heptane=7/1/0.1/5) gives the title compound as colourless crystals; m.p.: 209°–212°.

The starting materials may be prepared in the following manner:

A) 1-Amino-1-(5-chloro-2-pyridyl)-2-(1H-imidazol-1-yl)ethane a) 2-Acetyl-5-chloropyridine To a suspension of 56 g of 2-bromo-5-chloropyridine in 560 ml of dry diethylether is added a solution of 179 ml of n-butyllithium (15% solution in hexane) at −78° and under argon at such a rate that the temperature never exceeds −72°. Immediately thereafter the solution of 25.7 ml of N,N-dimethylacetamide in dry THF is added. The mixture is stirred for one hour at the same temperature and thereafter decomposed by careful addition of 100 ml of 3N hydrochloric acid, followed by 100 ml of water with vigorous cooling. Working up by process A (see Example 1) and purification by chromatogrphy over silica gel (toluene/ethyl acetate=20/1) yields the compound as white needles; m.p.: 58°–65°.

b) 2-Bromoacetyl-5-chloropyridine hydrobromide

To a solution of 10 g of 2-acetyl-5-chloropyridine in 150 ml of 48% aqueous hydrobromic acid are added 4 ml of bromine dissolved in 40 ml of hydrobromic acid, with stirring, drop by drop, at 80°. The mixture is stirred for additionally 3 hours at 80°. Afterwards the solution is evaporated in vacuo. The residue is triturated with acetone, filtered by suction, washed with acetone and dried in vacuo to yield yellow crystals of the compound, which is used for the next step without purification.

c) 2-[2'-(1H-Imidazol-1-yl)acetyl]-5-chloropyridine 15 g of 2-bromoacetyl-5-chloropyridine hydrobromide are dissolved in 50 ml of dry dichloromethane, 9.7 g of imidazole are added and the mixture is stirred for 24 hours at room temperature. Evaporation of the solvent in vacuo and subsequent chromatography of the residue over silicagel (dichloromethane/methanol/heptane=7/1/4) yield the compound as a cream coloured solid; m.p.: 122°–129°.

d) 1-(5-Chloro-2-pyridyl)-2-(1H-imidazol-1-yl)ethane-1-ol

A solution of 7.8 g of 2-[2'-(1H-imidazol-1-yl)acetyl]-5-chloropyridine in 40 ml of methanol is charged at 0°, in portions, with 2.0 g of sodium borohydride. The mixture is stirred for one hour at 0°. For working-up the mixture is decomposed by careful addition of 1N hydrochloric acid at 0°, followed by 1N sodium hydroxide to reach a pH of 9. The solvents are evaporated in vacuo. The residue is stirred with water and dichloromethane, the aqueous phase is extracted twice with dichloromethane and the combined organic extracts are washed with brine, dried and evaporated. The compound is obtained as a cream coloured solid; m.p.: >210° (decomp.). Purification is possible by chromatography over silicagel.

e) 1-Chloro-1-(5-chloro-2-pyridyl)-2-(1H-imidazol-1-yl)ethane 1 g of 1-(5-chloro-2-pyridyl)-2-(1H-imidazol-1-yl)ethane-1-ol is dissolved in 2 ml of toluene, 6 ml of thionyl chloride are added and the reaction mixture is stirred for 30 minutes at room temperature. The solvent and the thionyl chloride in excess are distilled off, the residue is dissolved in 2N NaOH, extracted with ethyl acetate, dried over $Na_2SO_4$ and evaporated to yield the compound as a colourless oil.

f) 1-Azido-1-(5-chloro-2-pyridyl)-2-(1H-imidazol-1-yl)ethane 0.92 g of 1-chloro-(5-chloro-2-pyridyl)-2-(1H-imidazol-1-yl)ethane are added under argon to a solution of 0.37 g of lithium azide in 2 ml of dry dimethylformamide and the reaction mixture is stirred at 60° for 18 hours. Working up according to process A (see Example 1) gives the substance as a yellowish oil.

g) 1-Amino-1-(5-chloro-2-pyridyl)-2-(1H-imidazol-1-yl)ethane

A solution of 0.83 g of 1-azido-1-(5-chloro-2-pyridyl)-2-(1H-imidazol-1-yl)ethane in 4 ml of dry pyridine is stirred under a $H_2S$-atmosphere for 3 hours. The reaction mixture is evaporated, the residue is redissolved in 5 ml of dilute acetic acid (acetic acid/water 1/4) and extracted with ethyl acetate. The combined organic phases are evaporated to give the title product as a yellowish oil.

Analogously as described above under A) the following starting materials of formula II are obtained as viscous yellowish oils, which are used without further purification (X=CH, $R_1$=H):

|    | $R_2$     | m.p. |
|----|-----------|------|
| B) | 2-pyridyl | oil  |
| C) | 3-pyridyl | oil  |
| D) | 4-pyridyl | oil  |

E) (S)-2-Phenyl-2-(1H-imidazol-1-yl)-1-aminoethane a) (R)-2-Amino-2-phenyl-ethanol-O-sulfate hydrogensulfate A solution of 10.65 g of (R)(−)-2-amino-2-phenylethanol in 30 ml of water is neutralized with 48% sulfuric acid to methyl red end point (4.2 ml), followed by addition of an equal volume of sulfuric acid. Water is then removed at a rotatory evaporator at 70°–90°, finally at 130° bath temperature and 0.1 Torr pressure to constant weight. The mixture gradually solidifies and is ground in a mortar. The material can be used without further purification for the next reaction.

b) (R)(−)-2-Phenyl-aziridine 16.2 g of finely ground (R)-2-amino-2-phenyl-ethanol-O-sulfate hydrogensulfate is added in portions to a stirred solution of 2N sodium hydroxide at 0°. The reaction mixture is then heated to 100° for 3 hours. For working up the mixture is cooled to room temperature and extracted four times with ether. The organic phase is washed with brine, dried over magnesium sulfate and evaporated. Distillation of the residue under reduced pressure yields the compound as a colourless oil; b.p.: 46° (0.1 Torr); $[\alpha]_D^{20}$=−46.7° (ethanol, c=1.09).

c) (S)-2-Phenyl-2-(1H-imidazol-1-yl)-1-aminoethane 1 g of (R)(−)-2-phenyl-aziridine and 1.14 g of imidazole are heated at 120° for 24 hours. After cooling the reaction mixture can be used for the acylating step without further purification. An analytical sample can be obtained by chromatography over silica gel;

$^1$H-NMR (CDCl$_3$) δ=7.66 (s; 1H), 7.41–7.31 (m; 3H), 7.24–7.18 (m; 2H), 7.11 (t, J=1 Hz; 1H), 7.03 (t, J=1 Hz; 1H), 5.17 (m; 1H), 3.43 (m; 2H), 2.60 (s, b; 2H).

F) N-(4'-Chlorobiphenyl-4-carbonyl)-2(R)-phenylaziridine

To a solution of 0.232 g of 4'-chlorobiphenyl-4-carboxylic acid in 3 ml of dry DMF, 0.18 g of N,N'-carbonyl-diimidazole are added with stirring at room temperature under argon atmosphere. After one hour a solution of 0.12 g of phenyl-aziridine in 0.5 ml of dry DMF is added dropwise. The reaction mixture is stirred for 21 hours and thereafter worked up as described in example 1. The compound is obtained as a pale yellow oil and used without purification in the next step.

G) 2-(4'-Chlorobiphenyl-4-yl)-5(S)-phenyl-4,5-dihydro oxazole a) 2-Amino-1(R)-phenyl-ethanol A solution of 15.8 g of R(−)-phenyloxirane in 150 ml of ethanol is cooled to −60° and 75 ml of ammonia are added. The reaction mixture is stirred for 70 hours at room temperature in a closed stainless steel reactor. The solvents are evaporated and 300 ml of water and 60 ml of toluene are added. Separation of the aqueous layer and removal of the solvent in vacuo yields 14.14 g of a colorless solid which contains 86% 2-amino-1(R)-phenyl-ethanol, 9% 2-amino-2-phenyl-ethanol and 5% 2-(2-hydroxy-2-phenylethylamino)-1-phenyl-ethanol (assessed by $^1$H-NMR). The mixture is used in the next step without further purification. Chromatography over silicagel (dichloromethane/methanol/28% aqueous ammonium hydroxyde=100/10/1) provides an analytical sample; m.p.: 64.6° (sublimes); $[\alpha]_D^{20}$=−44.3° (c=2, ethanol);

$^1$H-NMR (DMSO-d$_6$) δ=7.37–7.22 (m; 5H); 4.44 (dd, J=4.4, 7.7 Hz; 1H); 2.70/2.57 (ABX, J=11.3, 4.4, 7.7 Hz; 2H); 2.60 (bs; 3H).

b) 4'-Chlorobiphenyl-4-carbonyl-[2(R)-hydroxy-2-phenyl-ethyl]amide

A solution of 1.2 g of 4'-chlorobiphenyl-4-carboxylic acid and 715 μl of triethylamine in 20 ml of dry DMF is cooled to −20° and treated with 0.710 ml of isobutychloroformate. The reaction mixture is stirred for additionally 20 minutes and a solution of 955 mg crude (74%) 2-amino-1(R)-phenyl-ethanol in 5 ml of DMF is added. The mixture is allowed to come to room temperature and stirred for 16 hours. The slurry is poured onto 100 ml of ice-cold water, the precipitate is collected on a sinter funnel and washed three times with water and once with ethanol. Drying to constant weight yields the compound as pale yellow crystals; m.p.: 229.3°; $[\alpha]_D^{20}$=+48.1° (c=1.0, DMSO);

$^1$H-NMR (DMSO-d$_6$) δ=8.62 (t, J=5.6 Hz; 1H); 7.95/7.78/7.55 (3d, J=8.5 Hz; 8H); 7.41–7.22 (m; 5H); 5.55 (d, J=4.4 Hz; 1H); 4.81 (ddd, J=4.4, 4.7, 8.1 Hz; 1H); 3.56–3.46/3.40–3.29 (2m; 2H).

c) 2-(4'-Chlorobiphenyl-4-yl)-5(S)-phenyl-4,5-dihydro-oxazole

A solution of 1.24 g of 4'-chlorobiphenyl-4-carbonyl-[2(R)-hydroxy-2-phenylethyl]amide in 20 ml of pyridine is cooled in an ice bath and treated with a solution of 921 mg of methanesulfonic acid anhydride in dichloromethane. The reaction mixture is stirred for additional 16 hours at 5°, ethyl acetate and saturated aqueous sodium hydrogencarbonate are added, the organic layer is separated, dried and concentrated in vacuo. Vacuum flash chromatography on silica gel (toluene/ethyl acetate =3/1) yields the compound as pale yellow crystals; m.p.: 121.5° (recrystallized from ethanol); $[\alpha]_D^{20}$=+133.5° (c=1.3, methanol);
$^1$H-NMR (CDCl$_3$) δ=8.09/7.63/7.56/7.43 (4d, J=8.5 Hz; 8H); 7.44–7.36 (m; 5H); 5.68 (dd. J=7.9, 10.1 Hz, 1H); 4.51/4.02 (ABX, J=14.9, 10.1, 7.9 Hz; 2H).

H) (+) and (−)-1-Amino-1-(5-chloro-2-pyridyl)-2-(1H-imidazol-1-yl)ethane a) 1-[(1S)-Camphanoyl]amino-1-(5-chloro-2-pyridyl)-2-(1H-imidazol-1-yl)ethane To a solution of 0.38 g of 1-amino-1-(5-chloro-2-pyridyl)-2-(1H-imidazol-1-yl)ethane (racemic compound, see A) above) in 4 ml of dry dichloromethane is added 0.26 g (0.36 ml) of triethylamine. The mixture is stirred and cooled to −79°. Then 0.44 g of (1S)(−)-camphanic acid chloride are added in such a way that the temperature does not exceed −74°. Stirring is continued for additionally 90 minutes without further cooling. For working up the mixture is poured onto ice-water, extracted three times with dichloromethane and washed with brine. After drying with sodium sulfate the solvent is evaporated. A mixture of the two diastereomeric amides is obtained which is separated by chromatography over silica gel (dichloromethane/methanol/heptane=10/1/5). The two compounds are obtained as white crystals:
  diastereomer B: m.p.: 195°–199°
  diastereomer A: m.p.: 151°–160°.

b) (+)- and (−)-1-Amino-1-(5-chloro-2-pyridyl)-2-(1H-imidazol-1-yl)ethane 0.16 g of the camphanoyl diastereomer B are heated with 0.8 ml of 35% perchloric acid in a glass autoclave for 12 hours at 120°. After dilution with 2 ml of water the mixture is extracted with ethyl acetate (which is discarded). The aqueous phase is made alkaline with 2N sodium hydroxide and extracted three times with ethyl acetate. The organic layer is dried over magnesium sulfate and evaporated to dryness. Chromatography over silica gel (dichloromethane/methanol/heptane=10/1/5→7/1/4) yields the (+)-enantiomeric title compound (B isomer) as a pale yellow oil:
$^1$H-NMR (CDCl$_3$) δ=8.57 (d, J=2.5 Hz, 1H); 7.61 (dd, J, 2.5, J$_2$=8.3 Hz, 1H); 7.38 (s, 1H); 7.13 (d, J=8.3; 1H); 7.02 (s, 1H); 6.83 (s, 1H); 4.32–4.14 (m, 3H); 1.73 (s,b, 2H).

Analogously as described above the (−)-enantiomeric title compound (A isomer) is obtained by hydrolysis of the camphanoyl diastereoisomer A.

I) 2-Phenyl-2-(1H-imidazol-1-yl)-1-aminoethane

The compound is obtained from 2-phenylaziridine analogously as described above under E) c). Chromatography on silica gel (dichloromethane/methanol/aqueous NH$_3$=10/1/0.1 ) gives the title compound as a colourless viscous oil.

The compounds of formula I in free form or pharmacologically acceptable salt form, hereinafter briefly referred to as "the agents of the invention", exhibit pharmacological activity and are therefore useful as pharmaceuticals. In particular they are strong, selective inhibitors of the 25-hydroxyvitamin D3—hydroxylases, which attack the C20–27—side chain of calcitriol, e.g. the 25(OH)D3-24-hydroxylase, and thereby catabolize hormonally active vitamin D3—metabolites (e.g. calcitriol), while they interfere much more weakly with the synthesis of calcitriol itself, which occurs via the 25(OH)D3-1-hydroxylase.

Selective inhibition may e.g. be determined by the following test methods:
Activity of the 1-hydroxylase:
This can be determined in confluent cultures of human keratinocytes directly, while for determination of the activity of the hydroxylases attacking the C20–27—side chain a 16 hours pretreatment schedule of the confluent cultures with 1,25(OH)$_2$D3 (10 nM) has to precede which upregulates these activities (both methods are described in Bikle, D. D. et al., *J. Clin. Invest.* 78, 557 [1986]).
Keratinocyte cultures:
Normal human keratinocytes are isolated from fresh adult skin obtained from mammary reduction and immediately used under sterile conditions. Isolation and cultivation under serum-free conditions and without a feeder layer follows a modified protocoll as used by Bikle et al., *Biochemistry* 25 (1986) 1545–1548. These conditions are chosen in order to avoid undefined contributions from vitamin D—metabolites possibly retained in the serum and/or feeder layer. After separation of the epidermis from the dermis with a sterile dermatome the epidermis is incubated in a 0.25% trypsin solution for 45 minutes at 37°. Thereafter the cells are scraped off and put in 50 ml of HBSS containing 10% FCS to block further trypsin digestion and centrifuged at 2000 rpm for 2 minutes. The resulting cell pellet suspended in KGM, a defined serum-free medium at low (0.06 mM) calcium concentration containing 0.1 ng/ml EGF, 5 µg/ml insulin, 0.5 µg/ml hydrocortisone, bovine pituitary extract and antibiotics (gentamycin, amphothericin) gives the primary culture. After 24 hours at 37° in an incubator with carbogen gassing (95% O$_2$/5% CO$_2$) the unattached cells are removed, the flask washed and provided with fresh KGM. The culture medium is changed then every alternate day and the cells are passaged when they reach 80–90% confluency (usually 6 to 10 days after plating). For passaging old KGM is removed and the attached keratinocytes displaced by a short treatment (5 minutes) with 0.125% of trypsin, then put into HBSS+FCS, centrifuged and eventually resuspended in KGM in such a way that 1 plate of primary culture yields 3 plates first passage cells. In order to expand the final cell number keratinocytes are further cultivated as described above and generally used in their second passage.
a) Selective inhibition of Vitamin D3—hydroxylases:
Confluent cultures of human keratinocytes in KGM at low calcium (0.06 mM) have a high capacity to produce calcitriol via the 1-hydroxylase, however, activities of sequential metabolism via side chain oxidation are almost entirely lacking. Therefore, the inhibition of the 1-hydroxylase in the confluent cultures is determined directly, and the inhibition of sequential metabolism after up-regulation of the respective hydroxylases, e.g. the 24-hydroxylase, is determined by an overnight (17 hours) pretreatment with 10 nM of calcitriol as described by Bikle et al. (1986) (supra).

The activities of the 1-hydroxylase and of particular steps in the sequential metabolism [e.g. formation of 1,24, 25(OH)$_3$D3+1,24oxo,25(OH)$_2$D3] which still retain calcitriol-like activities, the formation of 3-epi calcitriol metabolites, of polar metabolites retained in the water phase and those indicative of side-chain cleavage and their inhibition by the test compounds are determined by following the oxidation of $^3$H-25(OH)D (Amersham; specific activity about 0.61 mCi/nmole) as follows:

Confluent human keratinocytes in 1 ml of KGM and in 6-well plates are incubated in duplicate at 37° with $^3$H-25(OH)D3 for 1 hour (1-hydroxylase), 4 hours (sequential metabolism) and for a range of time interals between 1 and 24 hours, without and after preincubation with 10 nM of calcitriol, and without and with test inhibitory compounds added in a concentration range between 0 and 10 μM. Thereafter, the reaction is stopped with 1 ml of methanol per well, the cells are scraped off, transferred to a test tube together with the supernatant and two washings (with 1 ml of methanol and 0.8 ml of water). Unmodified $^3$H-25(OH)D3 and most of the products are totally extracted from the combined solutions and the cell pellet by sequential extractions with 2.1 ml and 1 ml of $CHCl_3$ at room temperature. $^3$H-activity in the $CHCl_3$-phase, in the water, and total $^3$H-yield is determined. Incubations for extended time intervals (>4 hours) give rise to a high increase of $^3$H-activity in the water phase due to highly polar metabolites and a significant loss of $^3$H-activity in volatile products, almost entirely due to side chain cleavage in which the $^3$H-label at C26/27 is split off. The combined $CHCl_3$ extracts are then evaporated under argon at 35°, the residues dissolved in 0.4 ml of ethanol and an aliquot subjected to HPLC-analysis on a Zorbax-Sil column (Dupont; 4.6×250 mm) using a non-linear gradient from 97:3 to 85:15 of hexane:2-propanol at a flow rate of 2 ml/min and a total run time of 70 minutes. Substrate and individual metabolites are assigned to peaks by matching with unlabeled standards in co-chromatography. The extent of distinctive product formation in the presence of a particular inhibitor at concentrations ranging from 0 to 10 μM is determined and the strength of inhibition ($IC_{50}$) calculated from a Dixon Plot (1/rate versus inhibitor concentration). Selectivity can be assessed by comparing the $IC_{50}$ values of a distinct inhibitor for particular sequential processes and for the 1-hydroxylase.

b) $^3$H-Thymidine incorporation into human keratinocytes—antiproliferative effects of vitamin D—metabolites in the presence of selective inhibitors of their catabolism:

$^3$H-Thymidine incorporation is measured in 96-well plates as follows: Keratinocytes in 200 μl of KGM at low calcium concentration are plated at an initial density of $10^4$ cells per well (second passage) and kept for 24 hours at 37° in an incubator with carbogen gassing (95% $O_2$/5% $CO_2$). Thereafter, the test compounds are added in 1 μl of ethanol in a range of concentrations between 0 and 10 μM in the presence and absence of 25(OH)D3 or 1α,25(OH)$_2$D3 (both in a range between 0 and 7 nM), each concentration in triplicate. Blanks containing the solvent only or the vitamin D—metabolite are located after each well-triplet. 5 to 10 blanks per plate in the absence of solvent are added. After further 24 hours 50 μl of $^3$H-thymidine (1 μCi) in KGM are added, incubation continued for an additional 17 hours and eventually stopped by cell harvesting and lysis.

Harvesting is done on a Filtermate 196-Harvester (Packard-Canberra). In a first step, the supernatants are soaked through a 96-well filterplate and washed 3× with water. Measurement of these filterplates as described below clearly shows that no cells with incorporated $^3$H-activity have been shed off. Then the adherent cells in the incubated plates are released by treatment with 100 μl of 0.125% trypsin in PBS at 37° for 5 minutes, harvested on a new filterplate and washed 3× with water. 50 μl of scintillation cocktail (MicroScint O, Packard) are added and $^3$H-activity is counted on a Microplate Scintillation Counter (Topcount, Packard Canberra).

Data are used as means ±SEM (n=3). The $IC_{50}$-values for the inhibition of proliferation by the vitamin D—metabolites in the presence of varying concentrations of inhibitors of side chain metabolism and vice versa are assessed by plotting the inverse proliferation rate versus one inhibitor concentration, with the concentration of the other inhibitors kept constant (Dixon Plot). Independent of the mechanism of inhibition the $IC_{50}$-values can be read in this plot from the intercept on the x-axis.

The agents of the invention show inhibitory activity in the above tests a) and b) at concentrations of from about 0.01 μM to about 10 μM.

The agents of the invention are therefore useful as selective inhibitors of the 25-hydroxyvitamin D3—hydroxylases which attack the C20–27—side chain of vitamin D3, in the treatment of disorders of proliferation and differentiation in vitamin D—responsive tissues, particularly for the treatment of conditions where it is desired to selectively inhibit the catabolism of the hormone calcitriol without interfering with its synthesis from its precursor 25(OH)D3, such as to increase and prolong endogenous hormone levels and therefore exert beneficial effects with respect to proliferation and differentiation, to immune function and to calcium homeostasis, such as, for skin, in hyperproliferative and inflammatory diseases such as psoriasis and eczematous diseases, in degenerative changes of connective tissue both pathologic and accompanying normal aging, in the prevention of hair loss and regeneration of hair growth, and beyond skin, in tumor suppression, in increasing tolerance against allotransplantates, in rheumatoid arthritis and in bone remodeling.

For these indications the appropriate dosage will, of course, vary depending upon, for example, the agent of the invention used, the host, the mode of application and the intended indication. However, in general, satisfactory results in animals are indicated to be obtained at a daily dosage from about 1 mg/kg to about 20 mg/mg animal body weight. In larger mammals, for example humans, an indicated daily dosage is in the range from about 70 mg to about 1400 mg of an agent of the invention conveniently administered, for example, in divided doses up to two or four times daily for enteral/systemic treatment, and in the concentration range of less than 0.5%, e.g. 0.1%, to about 2% in a cream/solvent for topical treatment.

The agents of the invention may be admixed with conventional pharmaceutically acceptable diluents and carriers and, optionally, further excipients.

They may be administered by any conventional route, in particular enterally, e.g. orally, e.g. in the form of tablets or capsules, or topically, e.g. in the form of lotions, gels, creams, sprays and solutions such as ophthalmic or nasal solutions or aerosols for local treatment of skin and mucosal membranes, such as the eye, respiratory tract, vagina, oral and nasal cavity.

They may be administered alone or in combination with low doses of calcitriol or with standards such as cyclosporin A (Sandimmun®) to enhance immune suppressive and anti-inflammatory effects; far lower doses of the individual drugs than usual will reduce undesired side effects. The agents of the invention may substitute for therapy with glucocorticoids (e.g. dexamethasone, betamethasone, prednisolone) and other immune suppressive agents and may supplement treatment with calcitonin and parathyroidal hormone.

The enantiomeric compounds N-[4-(4-chlorophenyl)benzoyl]-2-(1H-imidazol-1-yl)-2(S)-phenyl-1-aminoethane (example 8) and its (R)-enantiomer (example 9), are the preferred agents in the above indications. They are selective inhibitors of the 25-hydroxyvitamin D3—hydroxylases which attack the C20–27—side chain of vitamin D3 without interfering with its synthesis from the precursor 25(OH)D3.

It has, for example, been determined that they have an $IC_{50}$ of between 10 nM and 50 nM in the above two tests a) and b) for the inhibition of side chain metabolism, e.g. for, respectively, the (S)- and the (R)-enantiomer:

in test a): 40 nM and 12 nM, respectively, as regards stabilization of 3-epi $1,25(OH)_2D3$ levels and 45 nM and 19 nM as regards stabilization of levels of the sum of $1,25(OH)_2D3$, $1,24,25(OH)_3D3$ and $1,24oxo,25(OH)_2D3$, but an $IC_{50}$ of 530 nM and 620 nM, respectively, for inhibition of 1-hydroxylase;

in test b): an $IC_{50}$ of 30 nM and 35 nM, respectively, as regards the concentration required to double the antiproliferative effect of $1\alpha,25(OH)_2D3$, and 11 nM and 12 nM for $25(OH)D3$.

It is, therefore, indicated that for treatment in e.g. psoriasis they may be administered at a concentration of from about 0.1% to about 0.5% by topical administration to large mammals, for example humans, by similar modes of administration as conventionally employed.

The invention also provides pharmaceutical compositions for e.g. topical application comprising an agent of the invention together with at least one pharmaceutically acceptable carrier or diluent. Such compositions may be manufactured in conventional manner by mixing an agent of the invention together with at least one pharmaceutically acceptable carrier or diluent. Unit dosage forms contain, for example, from about 20 mg to about 700 mg of active substance.

The use in the treatment of psoriasis is preferred.

The agents of the invention exhibit more pronounced and selective $25(OH)D3$—hydroxylase inhibiting activity than would be expected for structurally similar compounds.

We claim:

1. A compound of the formula

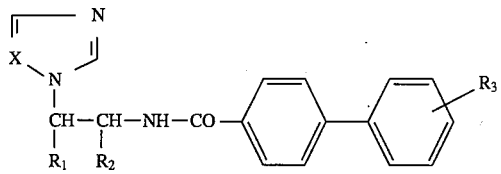

I wherein either $R_1$ is phenyl, naphthyl, thienyl or pyridyl, or phenyl, naphthyl, thienyl or pyridyl monosubstituted by halogen, $(C_{1-4})$alkoxy, $(C_{1-4})$alkyl, di-$(C_{1-4})$alkylamino or cyano and $R_2$ is hydrogen; or $R_1$ is hydrogen and $R_2$ is pyridyl or 2-(5-chloro)pyridyl;

$R_3$ is hydrogen, halogen, $(C_{1-4})$alkyl, $(C_{1-4})$ alkoxy, cyano, $(C_{1-4})$ alkoxycarbonyl, $(C_{1-4})$ alkylcarbonyl, amino or di-$(C_{1-4})$ alkylamino; and X is CH;

in free form or in salt form.

2. A compound according to claim 1 in free form.

3. A compound according to claim 1 in pharmacologically acceptable salt form.

4. A compound according to claim 1 of the formula

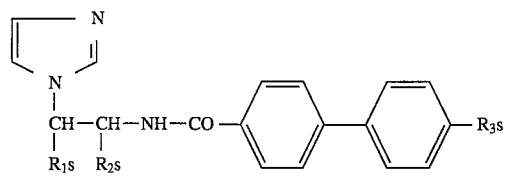

Is wherein either $R_1s$ is phenyl, phenyl monosubstituted by halogen, or 1-naphthyl, and $R_2s$ is hydrogen; or $R_1s$ is hydrogen and $R_2s$ is pyridyl or 2-(5-chloro)pyridyl; and $R_3s$ is halogen or $(C_{1-4})$alkoxy;

in free form or in pharmacologically acceptable salt form.

5. A compound according to claim 4 in free form.

6. A compound according to claim 1 of the formula

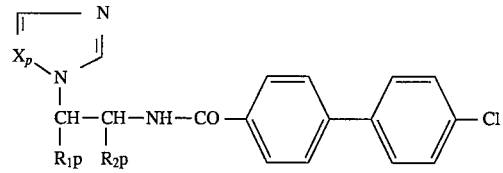

Ip wherein either $R_1p$ is phenyl, phenyl monosubstituted by chlorine in the 4-position, or 1-naphthyl, and $R_2p$ is hydrogen; or $R_1p$ is hydrogen, and $R_2p$ is 2-(5-chloro)pyridyl; and Xp is CH, in free form or pharmacologically acceptable acid addition salt form.

7. A compound according to claim 6 in free form.

8. The compound according to claim 1 which is N-[4-(4-chlorophenyl)benzoyl]-2-(1H-imidazol-1-yl)-2-phenyl-1-aminoethane in free form or pharmaceutically acceptable salt form.

9. The compound according to claim 8 in the form of the 2(S)-enantiomer in free form or pharmacologically acceptable salt form.

10. The compound according to claim 8 in the form of the 2(R)-enantiomer in free form or pharmacologically acceptable salt form.

11. A compound according to claim 1 wherein X represents CH and either $R_1$ represents hydrogen and $R_2$ and $R_3$ respectively represent 2-(5-chloro)pyridyl and 4-chloro, in racemic or (+)- or (−)-enantiomeric form, or represent 2-pyridyl and 4-chloro, or 3-pyridyl and 4-chloro, or 4-pyridyl and 4-chloro, or 2-(5-chloro)pyridyl and 4-ethoxy, or 2-(5-chloro)pyridyl and 4-n-butoxy;

or $R_2$ represents hydrogen, $R_3$ represents 4-chloro and $R_1$ represents 4-chlorophenyl, in racemic or (+)(S)-enantiomeric form, or represents 1-naphthyl;

in free form or pharmacologically acceptable salt form.

12. The compound according to claim 8 in free form.

13. The compound according to claim 9 in free form.

14. The compound according to claim 10 in free form.

15. A compound according to claim 11 in free form.

16. A pharmaceutical composition comprising a therapeutically effective amount of a compound of claim 1 in free form or in pharmacologically acceptable salt form and a pharmaceutically acceptable carrier or diluent therefor.

* * * * *